(12) United States Patent
Eriksson

(10) Patent No.: US 6,797,264 B1
(45) Date of Patent: Sep. 28, 2004

(54) MEDICINAL PRODUCT AND METHOD FOR TREATMENT OF CONDITIONS AFFECTING NEURAL STEM CELLS OR PROGENITOR CELLS

(75) Inventor: Peter Eriksson, Göteborg (SE)

(73) Assignee: Cellartis AB, Göteborg (SE)

( * ) Notice: Subject to any disclaimer, the term of this patent is extended or adjusted under 35 U.S.C. 154(b) by 0 days.

(21) Appl. No.: 09/856,576

(22) PCT Filed: Nov. 25, 1999

(86) PCT No.: PCT/SE99/02197

§ 371 (c)(1),
(2), (4) Date: Jul. 13, 2001

(87) PCT Pub. No.: WO00/30675

PCT Pub. Date: Jun. 2, 2000

(30) Foreign Application Priority Data

Nov. 25, 1998 (SE) .......................................... 9804064-5

(51) Int. Cl.$^7$ ........................ A61K 38/00; A61K 35/12; A61K 35/30

(52) U.S. Cl. ......................................... 424/93.1; 514/2

(58) Field of Search ................................ 424/93.1, 325, 424/366, 368, 198.1; 514/2; 435/325, 368, 405; 530/399

(56) References Cited

U.S. PATENT DOCUMENTS

| | | | | |
|---|---|---|---|---|
| 5,762,926 A | * | 6/1998 | Gage et al. | 424/93.21 |
| 5,851,832 A | * | 12/1998 | Weiss et al. | 435/368 |
| 5,980,885 A | * | 11/1999 | Weiss et al. | 424/93.21 |
| 6,284,539 B1 | * | 9/2001 | Bowen et al. | 435/455 |

FOREIGN PATENT DOCUMENTS

| | | |
|---|---|---|
| EP | 0324037 | 7/1989 |
| GB | 2 198 134 | 6/1988 |
| SE | 9804064-5 | * 11/1998 |
| WO | WO 88/05052 A1 | 7/1988 |
| WO | WO 90/12811 A1 | 11/1990 |
| WO | WO 92/04442 A1 | 3/1992 |
| WO | WO 94/10292 A1 | 5/1994 |
| WO | WO 94/22469 A1 | 10/1994 |
| WO | WO 96/15226 A1 | 5/1996 |

OTHER PUBLICATIONS

Ellis et al. (Dec. 1992) "A further British case of growth hormone induced Creutzfeldt–Jakob disease." Journal of Neurology, Neurosurgery, and Psychiatry 55(12): 1200–1202.*

Rossi and Cattaneo (May 2002) "Neural stem cell therapy for neurological diseases: dreams and reality." Nature Reviews 3: 401–409.*

Fricker–Gates et al. (2001) "Neural transplantation: Restoring complex circuitry in the striatum." Restorative Neurology and Neuroscience 19(1–2): 119–138.*

Ajo et al. (2003) "Growth Hormone Action on Proliferation and Differentiation of Cerebral Cortical Cells from Fetal Rat." Endocrinology 144(3): 1086–1097.*

Almazan et al. (Aug 1985) "Epidermal Growth Factor and Bovine Growth Hormone Stimulate Differentiation and Myelination of Brain Cell Aggregates in Culture." Developmental Brain Research 353(2): 257–264.*

Progress in *Neurobiology*, vol. 56, 1998, Stichel et al. "Experimental Strategies to Promote Axonal Regeneration After Traumatic Central Nervoic System Injury." pp. 119–148.

Growth Hormone MeSH search, http://www.ncbi.nlm.nih-.gov/entrez/query.fcgi?CMD=search&DB=mesh.

MeSH entry terms and categories for Growth Hormone, http://www.ncbi.nlm.nih.gov/entrez/query.fcgl?cmd=Retrieve&db=mesh&list_uids=mesh&list_uids=68013006&dopt=Full.

Growth Factor MeSH search, http://www.ncbi.nlm.nih.gov/entrez/query.fcgi?CMD =search&DB=mesh.

MeSH entry terms and categories for Growth Substances. http://www.ncbi.nlm.nih.gov/entrez/query.fcgi?cmd=Retrieve&db=mesh&list_uids=68016133&dopt=Full.

Nature, vol. 214, Jun. 10, 1967, Joseph Altman et al., "Postnatal Neurogenesis in the Guinea–pig", pp. 1098–1101.

J. Comp. Neur., V.S. Caviness, Jr. "Time of Neuron Origin in teh Hippocampus and Dentate Gyrus of Normal and Rooler Mutant Mice: An Autoradiographic Analysis", pp. 113–120. (1973).

Dev. Neurosci. 5: G. Gueneau et al., "Subgranular Zone of the Dentate Gyrus of Young Rabbits As a Secondary Matrix", A High–Resolution Autoradiographic Study, pp. 345–358 (1992).

(List continued on next page.)

*Primary Examiner*—Elizabeth Kemmerer
*Assistant Examiner*—Christopher James Nichols
(74) *Attorney, Agent, or Firm*—Burns, Doane, Swecker & Mathis, LLP

(57) ABSTRACT

Use of a substance that upon administration will lead to increased concentrations of growth hormone, such as growth hormone, a functionally equivalent analogue thereof or a substance that will increase the release of endogenous growth hormone, for the production of a medicinal product for treatment of abnormal conditions affecting neural stem cells, progenitor cells and/or cells derived from neural stem cells or progenitor cells, especially conditions affecting the oligodendroglia, astroglia, and/or neuronal cells. In vitro and in vivo methods for inducing lineage determination, propagating and/or inducing or maintaining the genesis of neurons, oligodendrocytes, astroglial cells from progenitor cells, stem cells and/or cells derived from said cells by administrating to the cells a substance that increases the concentration of growth hormone. Also a method of reducing the genesis of oligodendrocytes, neurons, astroglial cells from progenitor cells or stem cells, wherein a pharmaceutically effective amount of a substance that will lead to a decreased concentration of growth hormone or a functionally equivalent analogue thereof is administered to said patient.

13 Claims, 2 Drawing Sheets

OTHER PUBLICATIONS

The Journal of Neuroscience, Maryellen F. Eckenhoff et al., Nature and Fate of Proliferative Cells in the Hippocampal Dentate Gyrus DUring the Life Span of the Rhesus Monkey, pp. 2729–2747. (1988).

Nature Medicine, vol. 4, No. 11, Peter S. Ericsson et al. "Neurogenesis in the adult human hippocampus" pp. 1313–1317.

The Journal of Neuroscience, Mar. 15, 1996, H. Georg Kuhn et al., "Neurogenesis in the Dentate Gyrus of the Adult Rat: Age–Related Decrease of Neuronal Progenitor Proliferation", pp. 2027–2033.

Neuroscience vol. 56, No. 2, 1993, H.A. Cameron et al., "Differentiation of Newly Born Neurons and Glia in The Dentate Gyrus of the Adult Rat", Laboratory of Neuroendocrinology. The Rockefeler University, pp. 337–344.

The Journal of Neuroscience, Jun. 1993, Tatsunori Sekl et al., "High Polysialylated Neural Cell Adhesion Molecule (NCAM–H) is Expressed by Newly Generated Granule Cells in teh Dentate Gyrus of the Adult Rat" Department of Anatomy, Juntendo University School of Medicine, Tokyo 113, Japan, pp. 2351–2358.

The Journal of Neurosciences, vol. 4, No.6, Jun. 1984, Michael S. Kaplan et al., Mitotic Neuroblasts in The 9–Day–Old and 11–Month–Old Rodent Hippocampus, Department of Anatomy, University of New Mexico School of Medicine, pp. 1429–1441.

Brain Research. 611 (1993), Heather A. Cameron et al., "Adrenal Steroid receptor immunoreactivity in cells born in the adult rat dentrate gyrus", pp. 342–346.

Experimental Brain Research, B.B. Stanfield et al., Evidence that granule cells generated in the dentate gyrus of adult rats entend axonal projections, pp. 399–406. (1988).

Brian Research Reviews, 1993, Robert K. McNamara et al. The Neuropharmacoligical and neurochemical basis of place learning in the Morris water maze, pp. 33–49.

Neuroscience, vol. 61, No. 2, H.A. Cameron et al. "Adult Neurogenesis is Regulated by Adrenal Steroids in teh Dentate Gyrus", pp. 203–209. (1994).

Neuroscience vol. 82, No. 2, H.A. Cameron et al., "Adrenal Steroids and N–Methyl–D–Aspartate Receptor Activation Regulate Neurogenosis in The Dentate Gyrus of Adult Rats Through A Common Pathway", pp. 349–354. (1998).

Letters to Nature, Oct. 17, 1996, vol. 383, Janna O. Suhonen et al., "Differentiation of adult Hippocampus–rived progenitors into olfactory neurons in vivo". pp. 624–627.

Letters to Nature "More hippocampus neurons in adult mice living in an enriched environment" Gerd Kempermann et al., pp. 493–495. (1997).

J. Comp. Neur. 124, Joseph Altmen et al., autoradiographic and Hitological Evidence of Postnatal Hippocampal Neurogenesis in Rats, pp. 319–335 (1965).

Nyberg, Fred, "Aging Effects On Growth Hormone Receptor Binding In The Brain," Experimental Gerontology, 32(4/5), pp. 521–528, (1997), Elsevier Science, Inc. U.S.A.

* cited by examiner

MEDICINAL PRODUCT AND METHOD FOR TREATMENT OF CONDITIONS AFFECTING NEURAL STEM CELLS OR PROGENITOR CELLS

FIELD OF INVENTION

The present invention relates to use of substances that upon administration to a patient will lead to increased concentrations of growth hormone for the production of medicinal products.

The present invention also relates to a method for treatment of abnormal conditions affecting neural stem cells or progenitor cells.

BACKGROUND OF THE INVENTION

The result of traumatic, asfyxial, hypoxic, ischemic, toxic, infectious, degenerative or metabolic insults to the central nervous system (CNS) of man may involve a certain degree of damage in several different cell types. Damage to the brain by trauma, asphyxia, toxins, ischemia or infections are frequently causing neurological and cognitive deficits. Degenerative diseases may cause loss of specific populations of cells. For instance Parkinson's disease is associated by specific loss of dopaminergic neurons in the Substantia nigra, similarly, multiple sclerosis is associated with loss of myelin and oligodendrocytes. Other examples of degenerative disorders caused by selective loss of a specialized type of neurons is Alzheimer's disease associated with loss of cholinergic neurons. There are many other instances in which CNS injury or disease can cause damage to oligodendroglia, astroglia or neuronal cells.

Furthermore, axonal regeneration and sprouting after injury to axons in the CNS white mater tracts and injury to the spinal cord has been shown to be inhibited by surface molecules expressed by oligodendrocytes.

Progenitor cells have been grown and propagated with growth factors like epidermal growth factor (EGF), which is a substance belonging to a different class than GH.

In general, replacement of neurons following degeneration or damage is not a characteristic of the mammalian brain. Neuronal loss is thus considered permanent. Prolonged postnatal neurogenesis has been described in the granule cell layer of the hippocampal formation (Altman, J., and Das, G. D., J. Comp. Neurol. 124: 319–335 (1965); Altman, J. and Das, G. D. Nature 214: 1098–1101 (1967); Caviness, V. S. jr., J. Comp Neurol. 151: 113–120 (1973); Gueneau, G., Privat, A., Drouet, J., and Court, L., Dev. Neurosci. 5, 345–358 (1982); Eckenhoff, M. F., and Rakic, P., J. Neurosci. 8: 2729–2747 (1988)). Neurogenesis has recently been shown to persist well into adulthood in man (Eriksson, P. S., Perfilieva, E., Björk-Eriksson, T., Alborn, A., Nordborg, C., Peterson, D. A., Gage, F. H., Nature Med. in press). Neuronal progenitor cells reside in the subgranular zone (SGZ) of the dentate gyrus where they continuously proliferate, migrate into the granulae cell layer and differentiate into granule cells (Kuhn, H., Dickinson-Anson, H., and Gage, F. H., J. Neurosci. 16: 2027–2033 (1996); Cameron, H. A., Woolley, C. S., McEwen, B. S., and Gould, E., Neuroscience 56: 337–344 (1993); Seki, T. and Arai, Y., J. Neurosci. 13: 2351–2358 (1993)). These newborn neurons in the granule cell layer express markers of differentiated neurons and have morphological characteristics corresponding to differentiated granulae cells (Kaplan, M. S. and Bell, D. H., J. Neurosci. 4: 1429–1441 (1984); Cameron, H. A., Woolley, C. S., McEwen, B. S. and Gould, E. Neuroscience 56: 337–344 (1993); Cameron, H. A., Woolley, C. S., and Gould, E., Brain Res. 611: 342–346 (1993)). Furthermore, they establish axonal processes into the mossy fiber pathway and form synaptic connections with their targets in hippocampus CA3 (Seki, T. and Arai, Y., J. Neurosci. 13: 2351–2358 (1993); Stanfield, B. B. and Trice, J. E. Exp. Brain Res. 72: 399–406 (1988)). The hippocampus is associated with spatial learning and memory (McNamara, R. K, and Skelton, R. W., Brain Res. Rev. 18: 33–49 (1993)). The proliferation of progenitor cells can be influenced by the administration of n-methyl-d-aspartate (NMDA) receptor antagonists or by the removal of the adrenal glands (Cameron, H. A. and Gould, E. Neuroscience 61: 203–209 (1994); Cameron, H. A., Tanapat, P., and Gould, E., Neuroscience 82: 349–354 (1998)). Plasticity is reduced with increasing age, and recent studies have demonstrated that proliferation of progenitor cells also is decreased but not completely abolished with age (Kuhn, H., Dickinson-Anson, H., and Gage, F. H., J. Neurosci. 16: 2027–2033 (1996)). Stem cells isolated from the adult rodent brain has recently been transplanted into the brain of adult animals where they differentiate into cells with neuronal characteristics (Suhonen, J. O., Peterson, D. A., Ray, J. And Gage, F. H., Nature 383: 624–627 (1996)).

Furthermore, neurogenesis in the dentate gyrus in young mice has been shown to be facilitated by enriched environments. It was shown that exposure to enriched environments leads to an increased number of surviving newly formed granulae cell neurons and an increased total number of neurons in the dentate gyrus (Kempermann, G., Kuhn, H. G., and Gage, F. H., Nature 386: 493–495 (1997)).

SUMMARY OF THE INVENTION

It has now been found that by using growth hormone, or an analogue thereof, or another substance leading to increased concentrations of growth hormone or analogues thereof, it is possible to modulate the proliferation and/or differentiation of neural stem cells and progenitor cells from the adult CNS. The present invention thus provides new possibilities to treat injuries to or diseases of the central nervous system that predominantly affect oligodendroglia, astroglia or neuronal cells by modification of proliferation cell genesis and/or differentiation of neuronal stem cells or progenitor cells in the central nervous system.

It has also been found that it is possible to control the propagation in vitro of stem cells, progenitorcells and other cells, especially cells derived from the central nervous system, with the potential to generate neurons, astrocytes or oligodendrocytes. Such cells may e.g. be used for therapeutic purposes in patients.

Thus, the present invention relates to the use of a substance that upon administration to a patient will lead to an increased concentration of growth hormone or a functionally equivalent analogue thereof for the production of a medicinal product for treatment of an abnormal condition affecting neural stem cells and/or progenitor cells.

The invention also relates to a method for treatment of an abnormal condition affecting neural stem cells and/or progenitor cells, wherein a pharmaceutically active amount of a substance that will lead to an increased concentration of growth hormone or a functionally equivalent analogue thereof is administered to a patient.

Furthermore, the invention relates to a method of inducing lineage determination, propagating and/or inducing or maintaining the genesis of neurons, oligodendrocytes, astroglial cells from progenitor cells, stem cells and/or cells derived from said cells by administration of an effective amount of growth hormone or a functionally equivalent analogue thereof to stem cells, progenitor cells, neurons astroglial cells and/or oligodendrocytes in vitro.

Another aspect of the invention relates to abnormal conditions in the CNS due to too high concentrations of growth hormone in the CNS.

The invention thus also relates to the use of a substance that upon administration to a patient will lead to a decreased concentration of growth hormone or a functionally equivalent analogue thereof for the production of a medicinal product for treatment of an abnormal condition affecting stem cells, progenitor cells and/or cells derived from stem cells or progenitor cells, as well as to a method of reducing the genesis of oligodendrocytes, neurons, astroglial cells from progenitor cells or stem cells in, or derived from, the central or periferal nervous system in a patient, wherein a pharmaceutically effective amount of a substance that will lead to a decreased concentration of growth hormone or a functionally equivalent analogue thereof is administered to said patient. The characterizing features of the invention will be evident from the following description and the appended is claims.

DETAILED DESCRIPTION OF THE INVENTION

The mammalian brain, including the human brain, retains its ability to generate neurons throughout life in certain brain regions. New neurons and astroglial cells and oligodendrocytes are generated by cell genesis from stem or progenitor cells. During the research leading to the present invention it was found that growth hormone (below denoted GH) induces an increase in cell genesis from progenitors/stem cells in the adult brain. It was also found that increased number of new cells in the hippocampus is associated with improvement in learning and memory. These findings lead to the insight that it is possible to manipulate neurological deficits, such as memory and learning deficits, in patients by manipulating the amount of GH present in the environment surrounding the cells.

It was thus found that it is possible to treat a CNS damage or deficit after an insult by increasing the number of stem cells or progenitor derived cells including neurons, astroglial cells and oligodendrocytes.

It was also found that it is possible to treat neural loss suffered after a CNS insult by increasing the number of stem cells or progenitor derived cells including neurons, astroglial cells and oligodendrocytes in a patient by increasing the concentration of GH in the patient to induce proliferation and/or differentiation of stem cells with a concomitant increase in cell genesis.

Finally it was found that it is possible to treat neural loss suffered after a CNS insult by increasing the number of stem cells or progenitor derived cells including neurons and/or astroglial cells and/or oligodendrocytes in a patient by increasing the concentration of GH in the patient to induce proliferation and/or differentiation of stem cells with a concomitant increase in cell genesis in order to facilitate the isolation through surgical removal of small samples of brain tissue containing said cells for further expansion in vitro and concomitant re-transplantation into the patient.

Thus, the present invention relates to the use of a substance that upon administration to a patient will lead to an increased concentration of growth hormone, or of an analogue thereof, for the production of a medicinal product for treatment of an abnormal condition affecting neural stem cells, progenitor cells and/or cells derived from neural stem cells or progenitor cells, as well as to a method for treatment of an abnormal condition affecting neural stem cells, progenitor cells and/or cells derived from neural stem cells or progenitor cells, wherein a pharmaceutically active amount of a substance that will lead to an increased concentration of growth hormone is administered to a patient.

The substance that will lead to an increased concentration of growth hormone or analogue thereof may e.g. be growth hormone itself, or a functionally equivalent analogue thereof. The term "functionally equivalent analogue thereof" relates to all substances that upon administration to a patient will have essentially the same biological and pharmaceutical effect as GH. Such an analogue may e.g. be a synthetic GH mimetic. It is also possible to use a compound that upon administration to a patient will give rise to an elevated active concentration of GH or of a natural occurring GH analogue or its mediators in the CNS of the patient, e.g. by giving rise to an increased release of endogenous GH. For example, positively regulating binding proteins of GH may be used, such as the GH releasing substance growth hormone releasing peptide (GHRP) and analogous thereof.

The medicinal product according to the invention preferably comprises the active substance in a pharmacologically acceptable carrier or diluent such as those known in the art.

The medicinal product or the substance used according to the invention is preferably administered via intravenous periferal infusion or via intramuscular or subcutaneous injection into the patient. It is also possible to administer the medicinal product or the pharmaceutically active substance through a surgically inserted shunt into a cerebral ventricle of the patient.

Preferably, the administered subcutaneous dosage range of the pharmaceutically active substance is about 0.01-1 IE/kg body weight of the patient per week.

The term "patient", as used herein, relates to any human or non-human mammal in need of treatment according to the invention.

The term "treatment" used herein relates to both treatment in order to cure or alleviate a disease or a condition, and to treatment in order to prevent the development of a disease or a condition. The term treatment also refer to the affecting of cell genesis from stem cells or progenitor cells, by inducing the genesis of neurons and/or glial cells after either neuronal, oligodendroglial or glial cell loss in the CNS or PNS (periferal nervous system) or to prevent the normal age related deterioration in the CNS or PNS, the term also relates to the cultivation of stem or progenitor cells for concomitant transplantation to the CNS or PNS in patients. The treatment may either be performed in an acute or in a chronic way.

As stated above the pharmaceutically active substance used according to the invention is suitable for treatment of abnormal conditions affecting neural stem cells, progenitor cells and/or cells derived from neural stem cells or progenitor cells. It can thus be used to prevent, treat or ameliorate damages, diseases or deficits of central nervous system (CNTS). The pharmaceutically active substance used according to the invention is especially suitable for treatment of conditions affecting the oligodendroglia, astroglia, and/or neuronal cells. Such conditions may e.g. be a CNS damage or deficit, neuronal cell loss or memory loss. Such conditions may be caused by a number of different factors or diseases, such as multiple sclerosis, hypoxic injury, ischemic injury, traumatic injury, Parkinson's disease, and demyelition disorder.

The effect the pharmaceutically active substances used according to the invention is due to their ability to either induce cell genesis, proliferation and/or differentiation of progenitor derived cells in or from the central nervous system.

According to another embodiment of the invention it is possible to use growth hormone or a functionally equivalent analogue thereof in order to propagate progenitor cells or stem cells or other neural cells in a tissue culture or a cell culture. Such cells may thereafter be used for cell transplantation into a patient suffering from neuronal cell loss or a condition due to lack of endogenous cells of this type. The cells used to start the culture may either originate from the patient itself of from human or animal donors.

When cells are to be removed from a patient for in vitro propagation it may be advantageous to first increase the number of progenitor cells in the patient. This facilitating the subsequent isolation of said cells from patients facilitates the subsequent isolation of said cells from patients, The number of progenitor cells are increased by use of the method or medicinal product according to the invention, i.e. by the use of substance that upon administration to a patient will lead to an increased concentration of growth hormone or a functionally equivalent analogue thereof.

Growth hormone, or a functionally equivalent analogue thereof, may be used alone or in junction with other medicaments or growth factors such as epidermal growth factor (EGF) or fibroblast growth factor 2 (FGF2) designed to induce in cell genesis or proliferation in the CNS or PNS. Growth hormone, or a functionally equivalent analogue thereof, alone or in conjunction with other medicaments, peptides, growthfactors, steroids, lipids, glycosylated proteins or peptides, either simultaneous or in sequence, may be used in order to facilitate cell genesis or the generation of specific cell types in vivo or in vitro. It may also be used to induce immature, or multipotent cells to active specific developmental programs as well as specific genes in the aforementioned cells.

By the above mentioned cell genesis is meant the generation of new cells such as neurons oligodendrocytes schwancells and astroglial cells from multipotent cells, progenitor or stem cells within the adult CNS or PNS or in vitro.

Furthermore, the invention also relates to the therapeutic use of substances that decrease the amount of active GH or naturally occurring analogous of GH in the patient and thus decrease the genesis of oligodendrocytes in patients with axonal or spinal cord injury. Examples of such substances are negatively regulating binding proteins, GH-receptor antagonists, drugs or antibodies or compounds or peptides. Axonal regeneration and spinal cord injury have been shown to be inhibited by certain molecules expressed by oligodendrocytes. Furthermore, drugs or antibodies or compounds or peptides, that increase endogenous peptides, or proteins that decrease the biological activity of endogenous GH can also be used.

The invention will be more fully understood when reading the following example. It should not, however, be considered to limit the scope of the invention.

BRIEF DESCRIPTION OF THE DRAWINGS

In the examples below, reference is made to the appended drawings on which.

EXAMPLES

Figure 1:
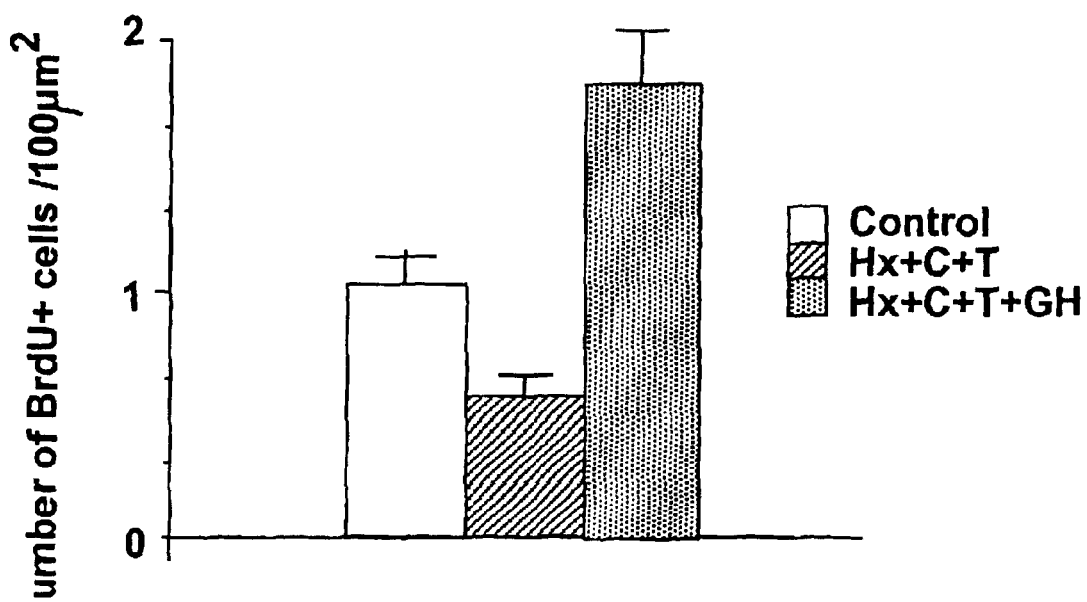
FIG. 1 shows the density of BrdU-positive cells after 7 days in the dentate gyrus of hypophysectomized (Hx) rats treated according to the invention with growth hormone (GH), together with cortisol (C), and L-thyroxine (T) compared to hypophysectomized rats treated with only C and T, and to a control group.

In this example, the density of BrdU-positive cells in the dentate gyrus of hypophysectomized (Hx) rate treated according to the invention with growth hormone (GH), cortisol (C), and L-thyroxine (T) was compared to the density of BrdU-positive cells in the dentate gyrus of hypophysectomized rats treated with cortisol (C), and L-thyroxine (T), and to the density of the same cells for an untreated unoperated control group.

Fisher rats (Harlan Sprague Dawley) which were inact or hypophysectomized at 50 days of age were mainained under standardized conditions of temperature (24–26° C.), humidity (50–60%) and with lights on between 0500 and 1900 h.

The rats had free access to standard laboratory chow and water. Hormonal treatment started 7–10 days after hyophysectomy. All the hypophysectomized rats were given cortisol phosphate (400 $\mu$g/kg/day; Solu-Cortef, Upjohn, Puurs, Belgium) and L-thyroxine (10 $\mu$g/kg/day; Sigma, USA) diluted in saline as a daily subcutaneous injection (at 0800 h). Recombinant bovine GH (bGH) was diluted in 0.05 M phosphate buffer, pH 8.6, with 1.6% glycerol and 0.02% sodium azide. GH 1 mg/kg/day was given as one daily subcutaneous injection at 24 h intervals. The treatment continued for seven days. Thereafter the rats were sacrificed and the brains taken out and prepared for immunohistochemistry.

Ten hypophysectomized rats were substituted with only cortisole and L-thyroxine. Fifteen hypophysectomized rats were substituted with cortisole, L-thyroxine and GH. Ten rats weighing 120 g were assigned to a control group. During the seven days of the treatment period all animals received a daily intraperitoneal injection (50 mg/kg bodyweight) of bromodeoxyuridine (BrdU; Sigma). The thymidine analog BrdU is incorporated into the genetic material upon mitotic division whereafter it can be detected immunohistochemically in the resulting cells. On the twentieth day all animals were sacrificed by a lethal dose of anesthetics and transcardially perfused with 4% paraformaldehyde. The brains were removed and postfixed in 4% paraformaldehyde for 24 h. and thereafter stored in 30% sucrose solution. Coronal freezing microtome sections (40 $\mu$m) were stored in cryoprotectant (25% ethylene glycol, 25% glycerin, 0.05 M phosphate buffer) at–20° C. until processing for immunohistochemistry or immunofluorescence.

The number of BrdU positive cells in the dentate gyrus of the hippocampus were counted using unbiased counting techniques. For detection of BrdU-labeled nuclei in tissue sections, the following DNA denaturation steps preceded the incubation with mouse anti-BrdU antibody 1:400 (Boeringer Mannheim): 2 h incubation in 50% formamide/2×SSC (0.3 M NaCl, 0.03 M sodium citrate) at 65° C., 5 min. Rinse in 2×SSC, 30 min incubation in 2N HCl at 37° C., and 10 min. Rinse in 0.1 M boric acid, pH 8,5. All stainings were performed on free floating 40 mm sections. Free-floating sections were treated with 0.6% $H_2O_2$ in tris buffered saline (TBS) (0.15M NaCl, 0.1M Tris-HCl, pH 7.5) for 30 min to block endogenous peroxidase. Several rinses in TBS were then followed by incubation in TBS/0.25% Triton X-100/3% normal horse serum (TBS-TS) for 30 min and incubation with primary antibody in TBS-TS overnight at 4° C. After rinsing in TBS-TS, the sections were incubated for 3 hr with biotinylated horse anti-mouse IgG, 1:160 secondary antibodies (Vector Laboratories, USA). After TBS rinsing avidin-biotin-peroxidase complex was applied for 1 h followed by peroxidase detection for 5 minutes (0.25 mg/ml diaminobenzidine, 0.01% $H_2O_2$, 0.04% NiCl).

For the immunofluorescence, sections were treated for DNA denaturation as described above, followed by incubation in TBS-TS for 30 min. Thereafter the sections were incubated with mouse-anti-Calbindin-D28k, 1:2000 (Sigma) for 16 h at 4° C. and was detected with a Texas red conjugated donkey anti-mouse IgG. BrdU was detected with a FITC conjugated rabbit anti-BrdU antibody. Fluorescent signals were detected and processed using a confocal scanning laser microscope (Bio-Rad MPC1024, Richmond, Calif).

The total number of BrdU positive cells in the granule cell layer, the subgranular layer and the hilus and their corresponding sample volumes were determined in 7–9 coronal sections, 240 mm apart, that contained the dentate gyrus. Cell counting was done according to an optical dissector method to avoid over sampling errors.

The results are shown in FIG. 1. After 7 days, the number of newborn cells in the dentate gyrus is significantly increased in hypophysectomized animals substituted with GH, cortisone, and thyroxine compared to animals substituted with only cortisone and thyroxine. Furthermore, the rate of proliferation was significantly increased after administration of GH to hypophysectomized animals treated with cortisol and L-thyroxine as quantified as after one week of substitution. These results clearly show that GH increase the proliferative rate of progenitor cells in the dentate gyrus in the hippocampus.

Furthermore, the rate of proliferation was significantly increased after administration of GH to hypophysectomized animals treated with cortisol and L-thyroxine as quantified after one week of substitution. This result suggest that GH affect the proliferative rate of progenitor cells in the dentate gyrus of the hippocampus.

Figure 2:
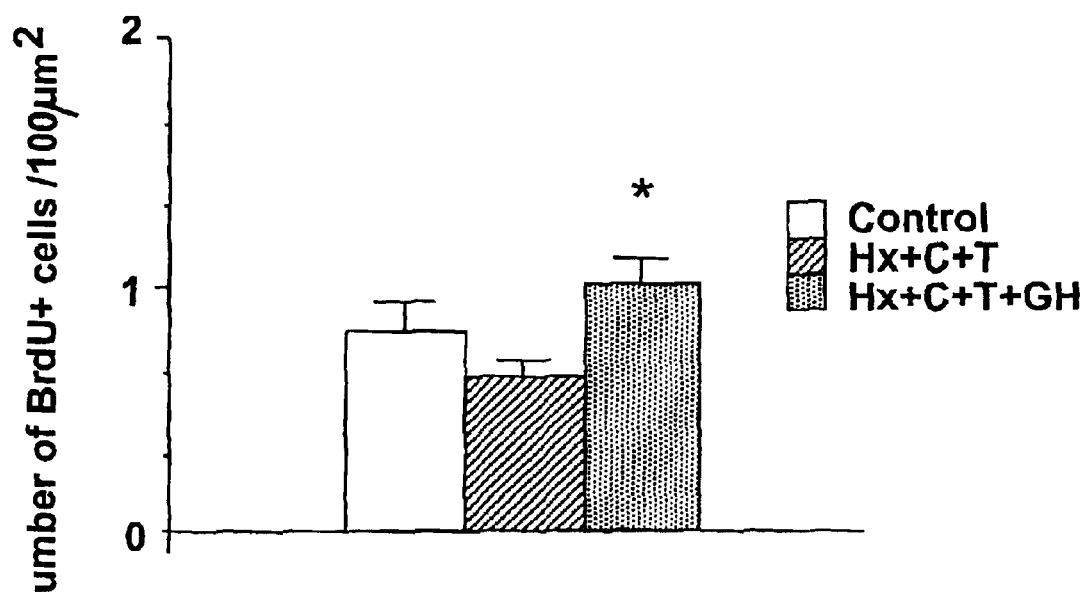
FIG. 2 shows that animals treated with cortisone, thyroxine and GH, according to the invention, had significantly more granulae cell neurons than hypophysectomized animals treated with only cortisone and thyroxine four weeks after the last BrdU injection the hypophysectomized animals

Furthermore, the proliferation was increased in normal animals receiving treatment for one week with GH compared with normal controls and compared with the hypophysectomized animals that were substituted for one week and thereafter unsubstituted during the following 3 weeks. The number of BrdU positive cells were estimated one month after treatment with either cortisone and L-thyroxine or cortisone, L-thyroxine and GH. The results are shown in FIG. 2.

The results suggest that GH either direct or indirect promote proliferation or survival of cells resulting from neural cell progenitor proliferation in the dentate gyrus.

The inventors of the present invention are the first to show that growth hormone can regulate the proliferation and subsequent generation of neurons in the adult brain.

Rats with increased number of newborn cells were tested and compared with rats that had lower number of newborn cells four weeks after BrdU injection during four consecutive days. The rats were tested in a water maze with a video-tracking system. The time to reach the platform (latency) were monitored. The escape platform was hidden 1 cm below the surface of the water at a fixed position. The water was made opaque by adding dry milk powder to the water. The water temperature was kept constant at 22° C. throughout the test. Each animal was tested in four trials each day. Each trial lasted 45 s. Animals that failed to find the hidden platform within 45 s were designated as having a 45-s latency and were put on the platform and allowed to stay there for 15 s.

Figure 3:
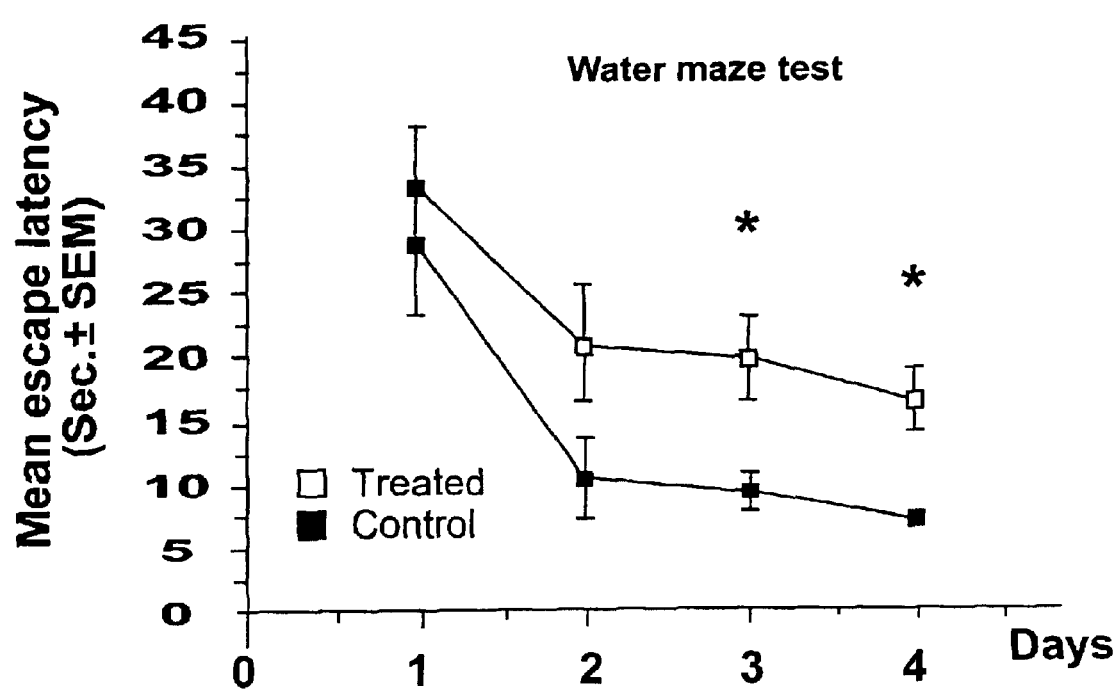
FIG. 3 shows that animals with increased number of new born cells according to the invention (⊖☐) performed significantly better in the hidden-platform version of the water maze task, used to assess spatial performance, than a control group (●■).

The latency in finding the platform during the water maze test was analyzed with a two-way ANOVA, and repeated postcomparative tests at each monitored time interval were performed using the Scheffe F-test. The results are shown in FIG. 3. There were no significant difference in swim speed. It is evident that animals with increased number of newborn cells in the dentate gyrus, due to treatment according to the invention, performed significantly better in the spatial learning task. These group of animals represent the data denoted with ⊖ ▭ in the figure. The data for the rats with the lower number of newborn cells are denoted with ● ■ in the figure.

What is claimed is:

1. A method of propagating cells selected from the group consisting of neuronal progenitor cells and neuronal stem cells in, or derived from, the central or peripheral nervous system in a mammalian patient in need of neuron propagation comprising:

(A) administering a composition comprising a pharmaceutically effective amount of mammalian growth hormone to said patient, wherein said pharmaceutically effective amount is effective to propagate neuronal progenitor cells and neuronal stem cells;

(B) removing brain cell from said patient;

(C) propagating said brain cell in vitro; and (D) transplanting the propagated brain cells into said patient.

2. A method of claim 1, wherein the growth hormone is further administered to said brain cells during in vitro propagation.

3. A method of claim 1, wherein the growth hormone comprising composition is administered by intravenous peripheral infusion or by intramuscular or subcutaneous injection.

4. A method of claim 2, wherein the growth hormone comprising composition is administered by subcutaneous injection.

5. A method of claim 2, wherein the growth hormone comprising composition is administered in a dosage of from about 0.01 to about 1 IU/kg body weight of the patient per week.

6. A method of any one of claims 1, 2, 3, or 4, wherein the composition comprises a further compound or composition capable of inducing cell genesis or proliferation is administered to said cells prior to removal from said patient.

7. A method of claim 6, wherein the further compound or composition are selected from the group consisting of peptides, growth factors, steroids, lipids, glycoslyated proteins, and combinations thereof.

8. A method of claim 7, wherein the further compound is a growth factor.

9. A method of claim 8, wherein the growth factor is epidermal growth factor or fibroblast growth factor 2.

10. A method of claim 9, wherein the combination of compounds or compositions is administered simultaneously.

11. A method of claim 10, wherein the combination of compounds or compositions is administered sequentially.

12. A method of claim 1, wherein the patient suffers from a condition associated with central nervous system damage or, neuronal cell loss.

13. A method of claim 12, wherein the neuronal cell loss is multiple sclerosis, hypoxic injury, ischemic injury, traumatic injury, Parkinson's disease, or a demyelination disorder.

* * * * *

UNITED STATES PATENT AND TRADEMARK OFFICE
CERTIFICATE OF CORRECTION

PATENT NO. : 6,797,264 B1
DATED : September 28, 2004
INVENTOR(S) : Peter Eriksson It is certified that error appears in the above-identified patent and that said Letters Patent is hereby corrected as shown below:

Column 8,
Lines 27 and 28, delete "cell" and insert -- cells --

Signed and Sealed this

Twenty-fifth Day of January, 2005

JON W. DUDAS
*Director of the United States Patent and Trademark Office*